(12) United States Patent
Bonda

(10) Patent No.: US 6,899,866 B2
(45) Date of Patent: May 31, 2005

(54) PHOTOSTABILIZATION OF A SUNSCREEN COMPOSITION WITH A COMBINATION OF AN α-CYANO-β, β-DIPHENYLACRYLATE COMPOUND AND A DIALKYL NAPHITHALATE

(75) Inventor: Craig A. Bonda, Winfield, IL (US)

(73) Assignee: CPH Innovations Corporation, Chicago, IL (US)

( * ) Notice: Subject to any disclaimer, the term of this patent is extended or adjusted under 35 U.S.C. 154(b) by 0 days.

(21) Appl. No.: 10/785,271

(22) Filed: Feb. 24, 2004

(65) Prior Publication Data

US 2004/0166072 A1 Aug. 26, 2004

Related U.S. Application Data

(63) Continuation-in-part of application No. PCT/US03/15841, filed on May 20, 2003, which is a continuation of application No. 10/361,223, filed on Feb. 10, 2003, which is a continuation-in-part of application No. 10/241,388, filed on Sep. 6, 2002, now abandoned.

(51) Int. Cl.$^7$ ............................. A61K 7/00; A61K 7/42; A61K 7/44

(52) U.S. Cl. ............................. 424/59; 424/60; 424/401
(58) Field of Search ............................. 424/401, 59, 60

(56) References Cited

U.S. PATENT DOCUMENTS

| | | | |
|---|---|---|---|
| 3,215,724 A | 11/1965 | Strobel et al. | 260/465 |
| 3,215,725 A | 11/1965 | Strobel et al. | 260/465 |

(Continued)

FOREIGN PATENT DOCUMENTS

| | | |
|---|---|---|
| CA | 1 164 886 | 4/1984 |
| CA | 2204430 | 5/1996 |
| DE | 31 06 071 | 2/1982 |
| DE | 44 40 055 | 5/1996 |
| DE | 195 19 895 | 12/1996 |
| DE | 10008895 | 8/2001 |
| DE | 100 15 863 | 10/2001 |
| DE | 100 26 628 | 12/2001 |
| DE | 100 58 290 | 5/2002 |
| EP | 0 675 875 | 11/1998 |
| EP | 0 900 782 | 3/1999 |
| EP | 1129696 | 9/2001 |
| EP | 1 308 084 | 5/2003 |
| JP | 56-140959 | 4/1981 |
| WO | WO 94/14760 | 7/1994 |
| WO | WO 96/15102 | 5/1996 |
| WO | WO 00/44340 | 8/2000 |
| WO | WO 01/16224 | 3/2001 |
| WO | WO 01/57125 | 8/2001 |
| WO | WO 01/90233 | 11/2001 |
| WO | WO 01/92395 | 12/2001 |
| WO | WO 02/42368 | 5/2002 |
| WO | WO 2004/031294 | 4/2004 |

OTHER PUBLICATIONS

"Photostability of HallStar Photostable SPF 32 Sunscreen Compared to Neutrogena UVA/UVB Sunblock SPF 30," Suncare Research Laboratories, Memphis, Tennessee (Oct. 5, 2000).
Beckwith, in "The chemistry of amides: Synthesis of amides," Zabicky, J., Ed. Interscience: New York, pp. 73–185 (1970).
Bentley et al., "Medium Effects on the Rates and Mechanisms of Solvolytic Reactions," *Adv. Phys. Org. Chem.*, vol. 14, pp. 1–67 (1977).
Bentley et al., "$Y_x$ Scales of Solvent Ionizing Power," *Progr. Phys. Org. Chem.*, vol. 17, pp. 121–158 (1990).
Dimroth et al., Über Pyridinium–N–Phenol–Betaine Und Ihre Verwendung Zur Charakterisierung Der Polarität Von Lösungsmitteln *Justus Liebigs Ann. Chem.*, vol. 661 pp. 1–37 (1963).
Fainberg et al., "Correlation of Solvolysis Rates. III. t–Butyl Chloride in a Wide Range of Solvent Mixtures," *J. Am Chem. Soc.*, vol. 78 pp. 2770–2777 (1956).
Grunwald et al., "The Correlation of Solvolysis Rates," J. Am. Chem. Soc., vol. 70, pp. 846–854 (1948).
Haslem, "Recent Developments in Methods For the Esterification and Protection of the Carboxyl Group," *Tetrahedron*, vol. 36, pp. 2409–2433 (1980).
Kamlet et al., "An Examination of Linear Solvation Energy Relationships," *Progr. Phys. Org. Chem.*, vol. 13, pp. 485–630 (1981).
Kosower, "The Effect of Solvent on Spectra. I. A New Empirical Measure of Solvent Polarity Z–Values," *J. Am Chem. Soc.*, vol. 80, pp. 3253–3260 (1958).
McNaught et al., "IUPAC Compendium of Chemical Terminology," $2^{nd}$ Ed. (1997).
Reichardt, "Solvents and Solvent Effects in Organic Chemistry," 2nd Ed., Chap. 7: Empirical Parameters of Solvent Polarity, VCH Publishers, New York, New York (1998).

(Continued)

Primary Examiner—Gary Kunz
Assistant Examiner—Marina Lamm
(74) Attorney, Agent, or Firm—Marshall, Gerstein & Borun LLP

(57) ABSTRACT

Sunscreen compositions including a dibenzoylmethane derivative, such as avobenzone, that are made more stable by the addition of (a) an α-cyano-β,β-diphenylacrylate compound, e.g., octocrylene and (b) a diester or polyester of naphthalene dicarboxylic acid (diethylhexyl 2,6-naphthalate), having a weight ratio of (a)/(b) of at least 0.95, preferably at least about 1.0. More particularly, the invention relates to sunscreen compositions which utilize a combination of octocrylene and diethylhexyl 2,6-naphthalate to stabilize other photoactive compounds present in a sunscreen composition and, in particular, to stabilize dibenzoylmethane derivatives, without, or with levels less than 0.5% by weight of, a methoxy-substituted benzophenone derivative, such as benzophenone-3.

32 Claims, No Drawings

U.S. PATENT DOCUMENTS

| | | | |
|---|---|---|---|
| 3,272,855 A | 9/1966 | Strobel et al. | 260/465 |
| 3,275,520 A | 9/1966 | Strobel et al. | 167/90 |
| 3,337,357 A | 8/1967 | Strobel et al. | 106/178 |
| 3,445,545 A | 5/1969 | Skoultchi | 260/881 |
| 3,992,356 A | 11/1976 | Jacquet et al. | 260/47 |
| 4,107,290 A | 8/1978 | Jacquet et al. | 424/47 |
| 4,128,536 A | 12/1978 | Brodsky et al. | 427/54 |
| 4,178,303 A | 12/1979 | Lorenz et al. | 260/465 |
| 4,202,834 A | 5/1980 | Gruber et al. | 260/465 |
| 4,202,836 A | 5/1980 | Gruber et al. | 260/465.4 |
| 4,203,919 A | 5/1980 | Gruber et al. | 260/465 |
| 4,207,253 A | 6/1980 | Lorenz et al. | 260/465 |
| 4,218,392 A | 8/1980 | Lorenz et al. | 260/465 |
| 4,247,475 A | 1/1981 | Ching | 260/465 |
| 4,260,719 A | 4/1981 | Ching | 528/196 |
| 4,263,366 A | 4/1981 | Lorenz et al. | 428/332 |
| 4,264,680 A | 4/1981 | Anthony | 428/412 |
| 4,276,136 A | 6/1981 | Gruber et al. | 204/159 |
| 4,387,089 A | 6/1983 | De Polo | 424/59 |
| 4,489,057 A | 12/1984 | Welters et al. | 424/47 |
| 4,562,067 A | 12/1985 | Hopp et al. | 424/59 |
| 4,868,246 A | 9/1989 | MacLeay et al. | 525/142 |
| 5,013,777 A | 5/1991 | MacLeay et al. | 524/159 |
| 5,096,977 A | 3/1992 | MacLeay et al. | 525/343 |
| 5,210,275 A | 5/1993 | Sabatelli | 560/43 |
| 5,321,112 A | 6/1994 | Olson | 528/75 |
| 5,576,354 A | 11/1996 | Deflandre et al. | 514/685 |
| 5,681,871 A | 10/1997 | Molock et al. | 523/106 |
| 5,821,380 A | 10/1998 | Holderbaum et al. | 558/443 |
| 5,869,099 A | 2/1999 | Keller et al. | 424/486 |
| 5,882,633 A | 3/1999 | Pisson et al. | 424/59 |
| 5,972,324 A | 10/1999 | Zofchak et al. | 424/78.03 |
| 5,993,789 A * | 11/1999 | Bonda et al. | 424/59 |
| 6,001,337 A | 12/1999 | Keller et al. | 424/59 |
| 6,033,649 A | 3/2000 | Gonzenbach et al. | 424/60 |
| 6,126,925 A | 10/2000 | Bonda et al. | 424/59 |
| 6,143,850 A | 11/2000 | Keller et al. | 526/304 |
| 6,284,916 B1 | 9/2001 | Bonda et al. | 560/80 |
| 6,297,300 B1 | 10/2001 | Van Nuffel | 524/91 |
| 6,306,507 B1 | 10/2001 | Brunelle et al. | 428/423.7 |
| 6,441,071 B1 | 8/2002 | Van Nuffel | 524/316 |
| 6,444,195 B1 * | 9/2002 | Cole et al. | 424/60 |
| 6,485,713 B1 * | 11/2002 | Bonda et al. | 424/59 |
| 6,491,901 B2 * | 12/2002 | Gers-Barlag et al. | 424/59 |
| 6,544,305 B2 | 4/2003 | Wood et al. | 44/275 |
| 6,555,095 B1 * | 4/2003 | Garrison | 424/59 |
| 6,610,409 B2 | 8/2003 | Pickett et al. | 428/423.7 |
| 6,689,474 B2 | 2/2004 | Pickett et al. | 428/423.7 |
| 2001/0022966 A1 * | 9/2001 | Gers-Barlag et al. | 424/59 |
| 2002/0194777 A1 | 12/2002 | Wood et al. | 44/275 |
| 2003/0000130 A1 | 1/2003 | Wood et al. | 44/275 |
| 2003/0069338 A1 | 4/2003 | Goossens et al. | 524/186 |
| 2003/0072945 A1 | 4/2003 | Pickett et al. | 428/412 |
| 2003/0130390 A1 | 7/2003 | Gorny et al. | 524/307 |
| 2003/0180542 A1 | 9/2003 | Pickett et al. | 428/423.7 |

OTHER PUBLICATIONS

Sayre et al., "Photostability Testing of Avobenzone," Allured's Cosmetics & Toiletries Magazine, vol. 114, No. 5, pp. 85–91 (May 1999).

Tarras–Wahlberg et al., "Changes in Ultraviolet Absorption of Sunscreens After Ultraviolet Radiation," *J. Investigative Dermatology*, vol. 113, No. 4, pp. 547–553 (1999).

Turro, *Modern Molecular Photochemistry* Benjamin/Cummings Publ. Co., Menlo Park, California, pp. 296–361 (1991).

* cited by examiner

PHOTOSTABILIZATION OF A SUNSCREEN COMPOSITION WITH A COMBINATION OF AN α-CYANO-β, β-DIPHENYLACRYLATE COMPOUND AND A DIALKYL NAPHITHALATE

CROSS-REFERENCE TO RELATED APPLICATION

This application is a continuation-in-part of application Ser. No. 10/361,223, filed Feb. 10, 2003, which is a continuation-in-part of application Ser. No. 10/241,388, filed Sep. 6, 2002, now abandoned.

BACKGROUND OF THE INVENTION

1. Field of the Invention

The invention relates to sunscreen compositions including a dibenzoylmethane derivative, such as avobenzone, that are made more stable by the addition of (a) an α-cyano-β,β-diphenylacrylate compound, e.g., octocrylene, and (b) a diester or polyester of naphthalene dicarboxylic acid (e.g., diethylhexyl 2,6-naphthalate), having a weight ratio of (a)/(b) of at least 0.95, preferably at least about 1.0. More particularly, the invention relates to sunscreen compositions which utilize a combination of octocrylene and diethylhexyl 2,6-naphthalate to stabilize other photoactive compounds present in a sunscreen composition and, in particular, to stabilize dibenzoylmethane derivatives, without, or with levels less than 0.5% by weight of, a methoxy-substituted benzophenone derivative, such as benzophenone-3.

2. Brief Description of Related Technology

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly-colored or sensitive skin, leading to reduction of skin elasticity and to wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to accept UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL® MCX, octyl salicylate, and oxybenzone.

The organic UV-A filters most commonly used in commercial sunscreen compositions are the dibenzoylmethane derivatives, particularly 4-(1,1 -dimethylethyl)-4'-methoxydibenzoylmethane (also called avobenzone, sold under the brand name PARSOL® 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above-described most commercially used UV-B filters.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy need to raise a photoactive compound to its excited state. For example, when avobenzone is combined with octyl methoxycinnamate, a bimolecular pathway leads to the rapid photodegradation of both the dibenzoylmethane derivative and the octyl methoxycinnamate.

Methods and compositions for stabilizing photoactive compounds, such as dibenzoylmethane derivatives, e.g., avobenzone, with diesters and/or polyesters of naphthalene dicarboxylic acid are described in U.S. Pat. Nos. 5,993,789, 6,284,916 and Gers-Barlag, et al. U.S. Pat. No. 6,491,901 ('901). Alternatively, Deflandre, et al., U.S. Pat. No. 5,576,354 and Gonzenbach et al., U.S. Pat. No. 6,033,649 describe the use of an α-cyano-β,β-diphenylacrylate compound, such as octocrylene, to stabilize a sunscreen composition including a dibenzoylmethane derivative. Thus, Deflandre et al. teach a minimum 1% by weight of octocrylene and Gonzenbach et al. teach a minimum of 0.5% by weight of octocrylene to stabilize a dibenzoylmethane derivative, such as avobenzone, in a sunscreen composition. Gers-Barlag, et al. U.S. Pat. No. 6,491,901 ('901) discloses sunscreen compositions containing a dibenzoylmethane derivative with a stabilizing combination of octocrylene and diesters or polyesters of naphthalene dicarboxylic acid wherein the examples have a weight ratio of octocrylene to the diester or polyester of naphthalene dicarboxylic acid in the range of 0.16 to 0.725, and the claims call for a weight ratio between about 0.03 and about 0.9.

In accordance with the '901 patent, the combination of octocrylene with one or more dialkyl naphthalates, according to the '901 invention, acts synergistically to prevent decomposition of avobenzone (see col. 4, lines 21–35). The combination of octocrylene and dialkyl naphthalates of the '901 patent, in the example formulations, disclose 1% to 2.9% octocrylene and 4% to 8% dialkyl naphthalate combinations.

In accordance with the compositions and methods described herein, it has been found that weight ratios of an α-cyano-β,β-diphenylacrylate, e.g., octocrylene, to diakyl naphthalate of at least 0.95, preferably at least about 1.0, provide surprisingly better results for photostabilizing a dibenzoylmethane derivative, such as avobenzone, than lower weight ratios, contrary to the teachings of the '901 patent.

In accordance with another embodiment of the compositions and methods described herein, the formulations contain 0% to about 10%, by weight, to less than 0.05% by weight benzophenone-3, more preferably about 0.1 to about 0.49% by weight benzophenone-3. By including benzophenone-3 in the formulation, a PA+++ rating UVA protection grade, as defined by the Technical Committee of the Japan Cosmetic Association (JCIA) in the Japanese Persistent Pigment Darkening Protocol, hereby incorporated by reference, and attached as an appendix to this application. It should be understood that benzophenone-3 in the formulations represents a separate, preferred embodiment, and is not necessary to provide excellent and surprising photostabilization of one or more dibenzoylmethane derivatives so long as the octocrylene/dialkyl naphthalate weight ratio is at least 0.95, preferably at least about 1.0, as shown in the examples.

SUMMARY

One aspect of the compositions and methods described herein is a composition including a mixture of a dibenzoylmethane derivative, and a combination of (a) an α-cyano-β,β-diphenylacrylate compound, such as octocrylene, and (b) a diester or polyester of naphthalene dicarboxylic acid, wherein the weight ration of (a)/(b) is at least 0.95, preferably at least about 1.0.

Another aspect of another embodiment of the compositions and methods described herein is a composition including a mixture of a dibenzoylmethane derivative, such as avobenzone, together with a combination of (a) an α-cyano-β,β-diphenylacrylate compound, such as octocrylene, (b) a diester or polyester of naphthalene dicarboxylic acid, wherein the weight ratio of (a) to (b) is at least 0.95, preferably at least about 1.0; and (c) 0 to about 3.0% by weight of benzophenone-3, preferably less than about 0.5% by weight benzophonone-3, more preferably about 0.1% by weight to about 0.49% by weight benzophenone-3.

Another aspect of another embodiment of the compositions and method described herein is a composition including a mixture of a dibenzoylmethane derivative, such as avobenzone, together with a combination of (a) an α-cyano-β,β-diphenylacrylate compound, such as octocrylene, (b) a diester or polyester of naphthalene dicarboxylic acid, wherein the weight ratio of (a) to (b) is at least 0.95, preferably at least about 1.0 and (c) a compound capable of raising the dielectric constant of an oil phase of the composition to a level of at least about 7.0 preferably at least about 8.0, such as dimethyl capramide and/or diethylhexyl malate.

Another aspect of the compositions and methods described herein is a composition including a mixture of (a) a dibenzoylmethane derivative, such as avobenzone, (b) an α-cyano-β,β-diphenylacrylate compound, such as oxybenzone, (c) a diester or polyester of naphthalene dicarboxylic acid, wherein the weight ratio of (b) to (c) is at least 0.95, preferably at least about 1.0; (d) 0 to bout 3.0% by weight of benzophenone-3, preferably less than about 0.5% by weight benzophonone-3, more preferably about 0.1% by weight to about 0.49% by weight benzophenone-3; and (e) a compound capable of raising the dielectric constant of an oil phase of the composition to a level of at least about 7.0 preferably at least about 8.0, such as dimethyl capramide and/or diethylhexyl malate.

Yet another aspect of the invention is a composition including a mixture of a dibenzoylmethane derivative, such as avobenzone, an α-cyano-β,β-diphenylacrylate compound, such as octocrylene, a diester or polyester of naphthalene dicarboxylic acid, and less than 0.5% benzophenone-3 capable of receiving a UVA protection grade of PA+++ (has a PFA—Protection Factor of UVA—of at least 8.0) when tested in accordance with the present Japanese Persistent Darkening Protocol.

DETAILED DESCRIPTION OF THE PREFERRED EMBODIMENTS

Sunscreen compositions containing a dibenzoylmethane derivative UV-A filter compound, such as 4-(1,1-dimethylethyl)-4'-methoxydibenzoylmethane (PARSOL® 1789) are photostabilized by containing (a) an α-cyano-β,β-diphenylacrylate compound, such as octocrylene; and (b) a diester or polyester of naphthalene dicarboxylic acid, wherein the weight ratio of (a)/(b) is at least 0.95, preferably at least about 1.0.

One aspect of the sunscreen compositions and methods described herein is to photostabilize a sunscreen composition containing a dibenzoylmethane derivative, such as avobenzone, by including in the composition a combination of (a) an α-cyano-β,β-diphenylacrylate compound, such as octocrylene, in an amount in the range of about 0.5% to about 8.0% by weight, preferably about 2% to about 7% by weight, more preferably about 1.5% to about 5% by weight, and (b) a diester or polyester of naphthalene dicarboxylic acid (DEHN), in an amount in the range of about 0.5% to about 8.0% by weight, preferably about 2% to about 7% by weight, more preferably about 1.5% to about 5% by weight, wherein the weight ratio of (a) to (b) is at lest 0.95, preferably at least about 1.0 to achieve a stable sunscreen composition.

In accordance with another embodiment of the sunscreen compositions and methods described herein, an α-cyano-β,β-diphenylacrylate compound is combined with a highly polar solvent or blend of solvents with a high polarity to enhance the photostabilizing effect of the α-cyano-β,β-diphenylacrylate compound, and thereby enhance the stability of the sunscreen composition.

In accordance with another embodiment of the compositions and methods described herein the photostabilizing effect of the diester or polyester of naphthalene dicarboxylic acid on the dibenzoylmethane derivative is enhanced by adding benzophenone-3, preferably at a level less than about 0.5% by weight.

A photoactive compound can be considered stable when, for example, after 30 MED irradiation the photoactive compound has retained at least 90% of its original absorbance at a wavelength or a range of wavelengths of interest (e.g., the wavelength at which or near a photoactive compound has a peak absorbance, such as 350–360 nm for avobenzone). Likewise, a sunscreen composition can include a plurality of photoactive compounds and a sunscreen composition, as a whole, can be considered stable when, for example, after 30 MED irradiation the sunscreen composition has retained at least 90% of its original absorbance at one or more wavelengths of interest (e.g., at or near the peak absorbance wavelength of the primary photoactive compounds).

It has surprisingly been found that the addition of (a) an α-cyano-β,β-diphenylacrylate compound, and (b) a diester or polyester of naphthalene dicarboxylic acid significantly increases the photostability of the sunscreen composition. Without intending to be limited to any particular mechanism of achieving this increase in stability, it is believed that a diester or polyester of naphthalene dicarboxylic acid stabilizes a dibenzoylmethane derivative by accepting the triplet is able to quench the excited state of a diester or polyester of naphthalene dicarboxylic acid, it is believed that the α-cyano-β,β-diphenylacrylate compound accepts the excited state energy and dissipates the energy kinetically in the form of rapid isomerizations. This process is shown below:

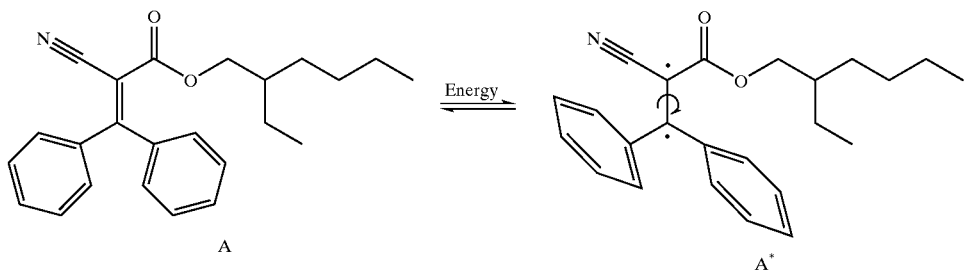

energy of the dibenzoylmethane derivative once the dibenzoylmethane derivative has reached an excited state as a result of the absorption of ultra-violet light. Once a dibenzoylmethane derivative is excited, it is prone to degrade according to a number of pathways, however, the degradation of the dibenzoylmethane derivative can be substantially reduced or prevented by the use of a diester or polyester of naphthalene dicarboxylic acid to quench (accept) the triplet excited state energy present in an excited dibenzoylmethane molecule. Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A diester or polyester of naphthalene dicarboxylic acid may stabilize a dibenzoylmethane derivative by accepting the triplet state (excited state) energy of the excited dibenzoylmethane derivative in such a way as to convert the excited dibenzoylmethane derivative back to a non-excited state that is capable of reaccepting ultra-violet radiation (energy transfer).

For this process to work continuously, the diester or polyester of naphthalene dicarboxylic acid must transfer or convert the energy that was accepted from the excited dibenzoylmethane derivative. Without intending to be limited to a particular mechanism, it is believed that when a diester or polyester of naphthalene dicarboxylic acid is excited to its triplet state, the triplet excited state energy is dissipated through vibrations (i.e., heat), which in this group of molecules is a slow mode of dissipating energy. It has been found, quite surprisingly, that by the addition of (a) an α-cyano-β,β-diphenylacrylate compound, together with (b) a diester or polyester of naphthalene dicarboxylic acid, in a weight ratio of (a)/(b) of at least 0.95, preferably at least 1.0, provides the α-cyano-β,β-diphenylacrylate compound with the capacity to accept triplet excited state energy from an excited diester or polyester of naphthalene dicarboxylic acid. Thus, according to one possible mechanism, the efficiency of the dissipation of the excited state energy in an excited diester or polyester of naphthalene dicarboxylic acid is greatly improved by a transfer of energy from an excited diester or polyester of naphthalene dicarboxylic acid to an α-cyano-β,β-diphenylacrylate compound.

Without intending to be limited to any particular mechanism by which an α-cyano-β,β-diphenylacrylate compound wherein the α-cyano-β,β-diphenylacrylate compound (octocrylene shown above as A), accepts the triplet excited state energy and forms a diradical (shown above as A*) at the α and β positions of the acrylate, which converts the double bond into a single bond and allows for the free rotation of the phenyl groups. This rotation occurs rapidly and efficiently to dissipate any excited state energy accepted by the α-cyano-β,β-diphenylacrylate compound. In solution (e.g., a sunscreen composition), a key limitation on one compound's ability to stabilize another is the ability of the two compounds to come into contact with one another. Thus, according to this mechanism of stabilization, it is preferred to have at least as much of the α-cyano-β,β-diphenylacrylate compound as the diester and/or polyester of naphthalene dicarboxylic acid so that the α-cyano-β,β-diphenylacrylate compound is abundant enough to quickly come into contact with an excited diester or polyester of naphthalene dicarboxylic acid.

Commonly-assigned U.S. Pat. No. 6,485,713 and application Ser. No. 10/092,131, the disclosures of which are hereby incorporated herein by reference, describe compositions and methods for increasing the stability of photoactive compounds in a sunscreen composition, e.g., by the addition of polar solvents to the oil phase of a composition. It has been found, quite surprisingly, that by increasing the polarity of the oil phase of a sunscreen composition including (a) an α-cyano-β,β-diphenylacrylate compound, and (b) a diester or polyester of naphthalene dicarboxylic acid, in a weight ratio of (a)/(b) of at least 0.95, preferably at least about 1.0, the stability of the sunscreen composition is increased. Now knowing that the polarity of the solution affects the stability, one might expect that the more polar the solution is, the greater the stability it will impart to the photoactive compound. In contrast, and even more surprisingly, it has been found that as the polarity of a solvent system including a dissolved, rapidly-photodegradable compound is increased, the rate of photodecay initially decreases—but then increases again as the polarity is further increased. Thus, a photodegradable compound in solution will degrade as a second-order function of the overall polarity of the solution. Currently accepted photochemical theory provides the possibility that the mechanism by which a photodegradable compound is stabilized is the transfer of a photonically-excited electron to a nearby molecule of the same or different species (see, e.g., N. J. Turro, Modem Molecular Photochemistry, Chapter 9, Benjamin/Cummings Publ. Co., Menlo Park, Calif. (1991)), however photochemical theory does not describe the observed phenomena. Though not intending to be bound by such a belief, the observed phenomena are believed to coincide with the electron transfer theory of Professor Rudolph A. Marcus of the California Institute of Technology, for which he received the 1992 Nobel Prize in Chemistry.

The dielectric constant of a solvent system is a preferred measure of polarity of a solvent system, for example because the dielectric constant is a measure of both inherent and inducible dipole moments. Other measures of polarity include, but are not limited to, the induced and/or inherent (permanent) dipole moment (e.g., in Debye units), the Dimroth-Reichardt $E_T$ parameter, and ionizing power. See generally, C. Reichardt, "Solvents and Solvent Effects in Organic Chemistry" 2nd ed., Chap. 7: Empirical Parameters of Solvent Polarity, VCH Publishers, New York, N.Y., (1988). Moreover, a more detailed description of these methods of measuring the polarity of the compound or a series of compounds can be found in commonly assigned U.S. patent application Ser. Nos. 10/092,131 and 10/092,132.

Mathematically, photodegradation can be described by an exponential function. Thus, Q(a), the absorbance after a radiation dose (i.e., exposure to a quantity of radiation), can be described by the general equation (i), $$Q(a)=Ae^{-kr} \qquad (i)$$

wherein A is the original (pre-exposure) absorbance, e is the natural logarithm base, k is the rate constant of the photodecay, and r is the cumulative dose (e.g., in MED units). Because the absorbance decreases as the cumulative dose increases (photodecay), the overall term –k will be negative, and the greater the value of –k (i.e., closer to zero) and, thus, the lower the rate constant of photodecay, the lower is the rate of photodecay. For example, when Q(a) is plotted on a log scale versus r on a linear scale, the function forms a straight line with a slope equal to –k.

Furthermore, it has been found that, for a set of photoactive compounds that includes a photodegradable compound (e.g. avobenzone), the rate constant of photodecay of the set of photoactive compounds can be described as a second-order function of the polarity, preferably the dielectric constant (i.e., relative permittivity) of the filter set dissolved in the solvent system. Thus, for example, the rate constant of photodecay of a filter set that include one or more of a photoactive compound, can be described by the general equation (ii), $$k=-(x\varepsilon^2+y\varepsilon+z) \qquad (ii)$$

wherein x, y, and z can be empirically determined. The dielectric constant at the theoretical minimum rate constant of photodecay –k min described by formula (iii), $$\varepsilon_{k\,min} = \frac{-y}{2x} \qquad (iii)$$

wherein x and y are defined as above.

The phenomena described above, coupled with the knowledge that, heretofore, sunscreen compositions have been formulated without specific regard to the relationship between polarity and photostability and, in newly-discovered fact, have had non-optimal polarities, forms the basis for at least one aspect of the compositions described herein.

A photoactive compound is one that responds to light photoelectrically. In the compositions disclosed herein, a photoactive compound is one that responds to UV radiation photoelectrically. For example, photoactive compounds that respond to UV radiation photoelectrically by rapid photo degradation can benefit highly from the compositions disclosed herein, even though the benefits of the compositions disclosed herein are not limited to such compounds. Photostability is a potential problem with all UV filters because they are deliberately selected as UV-absorbing molecules. In other applications, a photoactive compound may be a pigment or a dye (e.g., a hydrophobic dye).

UV filters include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid, and combinations thereof.

A sunscreen composition disclosed herein includes a dibenzoylmethane derivative. Preferred dibenzoylmethane derivatives include 2-methyldibenzoylmethane; 4-methyldibenzoylmethane; 4-isopropyldibenzoylmethane; 4-tert-butyldibenzoylmethane; 2,4-dimethyl- dibenzoylmethane; 2,5-dimethyldibenzoylmethane; 4,4'-diisopropyldibenzoylmethane; 4,4'-dimethoxy- dibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof. The compositions disclosed herein preferably include a dibenzoylmethane derivative in a range of about 0.1% to about 25% by weight of the total weight of the composition.

In any embodiment of a sunscreen composition an additional photoactive compound can be added to the composition. Additional photoactive compounds can be selected from any of the UV-A filters, UV-B filters, and combinations thereof. In a cosmetically-acceptable sunscreen embodiment for use on human skin, a photoactive compound preferably is selected from approved (if regulated), cosmetically-acceptable UV-A filters, UV-B filters, and combinations thereof.

For example, for a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3 diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds-and concentrations (percent by weight of the total cosmetic sunscreen composition) include diethanolamine methoxycinnamate (10% or less), ethyl-[bis (hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bis-benztriazolyl tetramethylbutylphenol (10% or less), disodium phenyl dibenzimidazole tetrasulfonate (10% or less, expressed as acid), bis-ethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine. (10% or less, also called TINOSORB S).

All of the above-described UV filters are commercially available. For example, suitable commercially-available organic UV filters are identified by trade name and supplier in Table 1 below:

TABLE I

| CTFA Name | Trade Name | Supplier |
| --- | --- | --- |
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |

As used herein, the term "alkyl" includes straight chained and branched hydrocarbon groups containing the indicated number of carbon atoms, typically methyl, ethyl, propyl, and butyl groups. The term "alkyl" also includes "bridged alkyl," e.g., a $C_4$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic hydrocarbon group, e.g., cyclopropyl, cyclobutyl, cyclohexyl, and cyclopentyl.

As used herein, the term "alkenyl" is defined identically as "alkyl," except for containing a carbon-carbon double bond. The term "cycloalkenyl" is identical to "cycloalkyl" except containing a carbon-carbon double bond, e.g., cyclopropyl, cyclobutyl, cyclohexyl, and cyclopentyl.

As used herein, the term "aryl," alone or in combination, is defined herein as a monocyclic or polycyclic aromatic group, preferably a monocyclic or bicyclic aromatic group, e.g., phenyl or naphthyl.

A sunscreen composition disclosed herein may include a variety of photoactive compounds, including one or more UV-A photoactive compounds and one or more UV-B photoactive compounds. Preferably, a sunscreen composition includes a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxynaphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3, 5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

A preferred combination of photoactive compounds in a sunscreen composition includes a UV-A and a UV-B photoactive compound. However, when 2-ethylhexyl-p-methoxycinnamate is included in a mixture with a dibenzoylmethane derivative, the dibenzoylmethane derivative becomes particularly unstable. Without intending to be limited to any particular mechanism, it is believed that the cinnamate ester reacts with an excited-state dibenzoylmethane derivative in a bimolecular pathway that renders both the dibenzoylmethane derivative and the cinnamate ester incapable of absorbing UV radiation.

It has been found, quite surprisingly, that a combination of (a) an α-cyano-β,β-diphenylacrylate compound and (b) a diester or polyester of naphthalene dicarboxylic acid in a weight ratio of (a)/(b) of at least 0.95, preferably at least about 1.0, increases the stability of a sunscreen composition including 2-ethylhexyl-p-methoxycinnamate and a dibenzoylmethane derivative. Thus, one embodiment of a sunscreen composition includes the photoactive compound 2-ethylhexyl-p-methoxycinnamate, a dibenzoylmethane derivative, and a combination of (a) and (b) in weight ratios previously defined.

It has been found, quite surprisingly, that the addition of a methoxy-substituted benzophenone derivative to a sunscreen composition including a dibenzoylmethane derivative and a diester or polyester of naphthalene dicarboxylic acid results in an increase in the stability of the dibenzoylmethane derivative present in the composition. A methoxy-substituted benzophenone derivative has dual purposes in the sunscreen composition, both to act as a photoactive compound, and to increase the photostability (lower the rate constant of photodecay) of one or more photoactive compounds present in the sunscreen composition. Without intending to be limited to any particular mechanism, it is believed that a methoxy-substituted benzophenone derivative quenches (accepts) the singlet excited state of the diester or polyester of naphthalene dicarboxylic acid, and thereby prevents the excited diester or polyester from reaching the triplet excited state. Preferably, a sunscreen composition disclosed herein includes a methoxy-substituted benzophenone derivative such as benzophenone-3. The methoxy-substituted benzophenone derivative preferably is present in a sunscreen composition in an amount of 0.5% or less by weight of the total weight of the composition.

One embodiment of a sunscreen composition disclosed herein includes a mixture of a dibenzoylmethane derivative, and a weight ratio of (a)/(b) of at least 0.95, preferably at least about 1.0, wherein (a) is an α-cyano-β,β-diphenylacrylate compound, and (b) is a diester or polyester of naphthalene dicarboxylic acid selected from the group consisting of formula (I), formula (II), and combinations thereof:

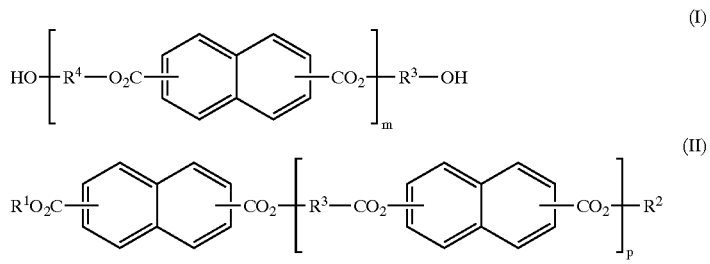

wherein $R^1$ and $R^2$ are the same or different and selected from the group consisting of $C_1$–$C_{22}$ alkyl groups, diols having the structure HO—$R^3$—OH, and polyglycols having the structure HO—$R^4$—(—O—$R^3$—)$_n$—OH; wherein each $R^3$ and $R^4$ is the same or different and selected from the group consisting of $C_1$–$C_6$ straight or branched chain alkyl groups; and wherein m and n are each in a range of 1 to 100 and p is in a range of 0 to 100. Although any α-cyano-β,β-diphenylacrylate compound may be used in this embodiment, preferably, the α-cyano-β,β-diphenylacrylate compound is 2-ethylhexyl-2-cyano-3,3-diphenylacrylate (also known as octocrylene).

The method of preparation of particularly useful diesters and polyesters of naphthalene dicarboxylic acid and the use of diesters and polyesters of naphthalene dicarboxylic acid in a sunscreen composition are described in U.S. Pat. Nos. 5,993,789 and 6,284,916, the disclosures of which are hereby incorporated herein by reference. Preferably, a composition of this embodiment includes a diester of formula (II) wherein $R^1$ and $R^2$ are 2-ethylhexane and p is 0. Preferably, the compositions disclosed herein include a diester or polyester of naphthalene dicarboxylic acid in a range of about 0.1% to about 15% by weight of the total weight of the composition.

As described above, the stability of photoactive compounds present in a sunscreen composition can be increased by controlling the polarity of the oil phase of the composition. Because prior sunscreen formulations have typically had lower than optimal polarities, adding a high-polarity component to the oil phase to raise the oil phase polarity improves the photostability of the photoactive compounds. Thus, preferably, a sunscreen composition includes an oil phase comprising a dibenzoylmethane derivative, (a) an α-cyano-β,β-diphenylacrylate compound, (b) a diester or polyester of naphthalene dicarboxylic acid, in a weight ratio of (a)/(b) of at least 0.95, preferably at least about 1.0, and a solvent system, wherein the solvent system includes an effective amount of a polar solvent, or a blend solvents with a high polarity, to increase the photostability of the dibenzoylmethane derivative or other photoactive compounds present in the sunscreen composition. Suitable polar solvents for use in a sunscreen composition are disclosed in commonly assigned U.S. patent application Ser. Nos. 10/097,131 and 10/092,132, the disclosures of which are hereby incorporated herein by reference. A composition of this embodiment preferably has a dielectric constant of at least 7, preferably at least about 8.

Another embodiment of the sunscreen compositions disclosed herein includes a mixture of a dibenzoylmethane derivative, (a) an β-cyano-β,β-diphenylacrylate compound, (b) a diester or polyester of naphthalene dicarboxylic acid, in a weight ratio of (a)/(b) of at least 0.95, preferably at least about 1.0, and (c) benzophenone-3 in an amount of about 0.1 to 10% by weight, preferably less than about 0.5% by weight. Although any α-cyano-β,β-diphenylacrylate compound may be used according to this embodiment, preferably, the α-cyano-β,β-diphenylacrylate compound is 2-ethylhexyl-2-cyano-3,3-diphenylacrylate (also known as octocrylene).

Another embodiment of a sunscreen composition disclosed herein includes a mixture of a dibenzoylmethane derivative, (a) an α-cyano-β,β-diphenylacrylate compound, and (b) a diester or polyester of naphthalene dicarboxylic acid, in a weight ratio of (a)/(b) of at least 0.95, preferably at least about 1.0, wherein said sunscreen composition has a dielectric constant of at least about 8.

EXAMPLES

The following examples are provided to illustrate the invention but are not intended to limit the scope of the invention.

Two sunscreen compositions were produced by mixing the ingredients and concentrations (formulations) shown in the following two examples:

Example 1

| | | In vivo PFA 8.63 | |
|---|---|---|---|
| Phase | INCI/CTFA Chemical Name | Trade Name, Supplier | % w/w |
| A. | Octisalate | (USP, RTD*HALL STAR) | 5.00 |
| | Homosalate | (NeoHeliopan HMS, Symrise) | 7.50 |
| | Avobenzone | (Parsol 1789, Roche) | 3.00 |
| | Octocrylene | (NeoHeliopan 303, Symrise) | 2.50 |
| | Diethylhexyl 2,6-naphthalate | (Symrise) | 2.50 |
| | Dimethyl capramide | (Spectrasolv DMDA, RTD*HALLSTAR) | 1.00 |
| | Diethylhexyl malate | (Spectrasolv 16, RTD*HALLSTAR) | 2.01 |
| | Benzophenone-3 | (NeoHeliopan BB, Symrise) | 0.49 |
| B. | Polyglyceryl-3 distearate | (Cremorphor GS-32, BASF) | 3.00 |
| | Sorbitan isostearate | (Crill 6, Croda) | 4.00 |
| | Stearic acid | (V-1655, RTD*HALLSTAR) | 3.05 |
| | PVP/Eicosene copolymer | (Ganex V-220, ISP) | 2.00 |
| | Dimethicone (100 cSt) | (Mirasil DM100, RTD*HALLSTAR) | 0.40 |
| | Silica | (R972, Degussa) | 0.25 |
| C. | Deionized water | Water | Q.S. |
| | Disodium EDTA | Disodium EDTA | 0.05 |
| | Carbomer | (Carbopol Ultrez 10, B. F. Goodrich) | 0.05 |
| D. | Methylpropanediol | (MPDiol, Lyondell) | 2.00 |
| | Glycerin | Glycerin | 3.00 |
| | Phenoxyethanol()methyl-paraben()ethylparaben()propyl-paraben()butylparaben | (CoSept PEP, RTD*HALLSTAR) | 0.60 |
| | Triethanolamine (TEA) | Triethanolamine | 1.74 |

Procedure
1. Oil Phase: Blend "A" liquid additives. Heat to 80° C., stirring to dissolve Oxybenzone, Avobenzone. Add "B" additives with stirring until clear and homogeneous.
NOTE: Addition of Dimethicone will turn oil phase turbid. Add silica and stir to wet and disperse thoroughly.
2. Water Phase: Dissolve EDTA salt in water. Sprinkle carbomer on water and allow to wet completely. With stirring, heat to 75° C. Preblend preservative, Methylpropanediol, Glycerin, and TEA, and add to water.
3. With stirring, add oil ("A" + "B") to water ("C" + "D"). A crude yellowish emulsion will form. Remove from heat. Continue stirring until temperature falls below 75° C. Homogenize for three minutes to form a white, fine emulsion. Switch to sweep. Stir while cooling. Package when temperature drops below 35° C.
4. Don't forget to add back water lost during processing.

The following in-vivo PFA values were obtained from using the composition of Example 1 on five individuals, in accordance with the Japanese Pigment Darkening Protocol (Appendix):

TABLE II

Individual PFA Values

| Subject | CPTC# | Skin Type | Age/Sex | 180 Minutes Standard | CAB4-269 |
|---|---|---|---|---|---|
| 1) JA | 38973 | IV | 54/M | 5.86 | 9.38 |
| 2) BB | 38974 | III | 54/F | 4.68 | 7.50 |
| 3) RA | 388912 | III | 26/M | 5.86 | 9.38 |
| 4) TF | 40813 | III | 19/M | 4.69 | 7.50 |
| 5) NF | 12775 | III | 56/M | 4.69 | 9.38 |
| Average PFA (N = 5) | | | | 5.16 | 8.63 |

Example 2

The following composition was produced and tested for photostability in the same manner described with reference to Example 1, above. The addition of 0.20% by weight diethylhexyl malate to the control was to maintain identical oil phase volumes in all formulations tested. The sunscreen compositions included very low ratios of octocrylene (OC) to DEHN (diester or polyester of naphthalene dicarboxylic acid) of 0.06 and 0.026.

In vivo PFA 7.27

| Phase | INCI/CTFA Chemical Name | Trade Name, Supplier | % w/w |
|---|---|---|---|
| A. | Octisalate | (USP, RTD*HALL STAR) | 5.00 |
| | Homosalate | (NeoHeliopan HMS, Symrise) | 7.25 |
| | Avobenzone | (NeoHeliopan 357, Symrise) | 3.00 |
| | Octocrylene | (NeoHeliopan 303, Symrise) | 0.26 |
| | Diethylhexyl 2,6-naphthalate | (Symrise) | 10.0 |
| | Dimethyl capramide | (Spectrasolv ® DMDA, RTD*HALLSTAR | 0.49 |
| B. | Stearyl alcohol | (Alfol 18, Sasol) | 1.00 |
| | Polyglyceryl-3 methyl glucose distearate | (TegoCare 450, Goldschmidt) | 3.00 |
| | Steareth-21 | (Brij 721, Uniqema) | 0.31 |
| | Steareth-2 | (Brij 721, Uniqema) | 0.19 |
| | C30–38 Olefin/Isopropyl maleate/MA copolymer | (Performa V 1608, New Phase) | 2.00 |
| C. | Deionized water | Water | Q.S. |
| | Disodium EDTA | Disodium EDTA | 0.05 |
| D. | Glycerin | Glycerin | 4.00 |
| | Phenoxyethanol()methyl-paraben()ethylparaben()propyl-paraben()butylparaben | (Phenonip, Clariant) | 0.60 |
| E. | Carbomer | (Carbopol Ultrez 10, B. F. Goodrich) | 0.20 |
| F. | Sodium hydroxide (25%) | Sodium hydroxide | 0.28 |

Procedure
1. Oil Phase: In secondary vessel, blend "A" liquid additives. Heat to 80° C., stirring to dissolve Oxybenzone, Avobenzone. Increase heat to 90° C. Add "B" additives with stirring until clear and homogeneous.
2. Water Phase: In small vessel, pre-disperse carbomer ("E") in water (15–20 parts water to 1 part carbomer; allow to sit for 15–20 minutes) and set aside. Charge primary vessel with water (less amount of water used to pre-disperse carbomer). Dissolve Disodium EDTA in water. Heat to 85° C. Pre-blend preservative, Glycerin and add to water. Stir to disperse.
3. With homogenization, add oil ("A" + "B") to water ("C" + "D"). While continuing to homogenize, add pre-dispersed carbomer ("E"). Maintain heat at 80–90° C., homogenize for 2 minutes.
4. Remove from heat. Stir with sweep while cooling. When temperature is below 40° C. slowly neutralize with Sodium hydroxide ("F") solution to pH 6–6.5. Continue stirring to smooth, homogenous lotion.
NOTE:
Be sure to add back any water lost during processing.

What is claimed is:

1. A sunscreen composition, comprising a mixture of a dibenzoylmethane derivative, with (a) an α-cyano-β,β-diphenylacrylate compound, and (b) a diester or polyester of naphthalene dicarboxylic acid selected from the group consisting of formula (I), formula (II), and combinations thereof:

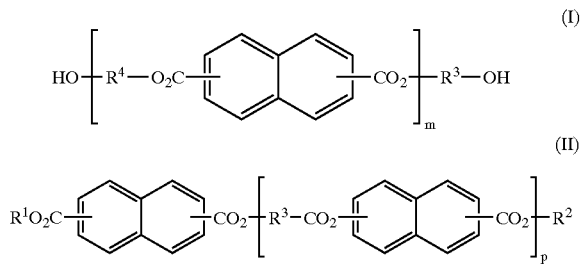

wherein $R^1$ and $R^2$ are the same or different and selected from the group consisting of $C_1$–$C_{22}$ alkyl groups, diols having the structure HO—$R^3$—OH, and polyglycols having the structure HO—$R^4$—(—O—$R^3$—)$_n$—OH; wherein each $R^3$ and $R^4$ is the same or different and selected from the group consisting of $C_1$–$C_6$ straight or branched chain alkyl groups; wherein m and n are each in a range of 1 to 100 and p is in a range of 0 to 100; wherein the weight ratio of (a)/(b) is at least 0.95.

2. The composition of claim 1, wherein the weight ratio of (a) to (b) is at least about 1.0.

3. The composition of claim 2, further including a methoxy-substituted benzophenone derivative in an amount of about 0.1% by weight to about 10% by weight of the sunscreen composition.

4. The composition of claim 3, wherein the methoxy-substituted benzophenone derivative is benzophenone-3, included in the sunscreen composition in an amount less than about 0.5% by weight.

5. The composition of claim 1, wherein said dibenzoylmethane derivative is selected from the group consisting of 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

6. The composition of claim 1, wherein said dibenzoylmethane derivative is present in a range of about 0.1% to about 25% by weight of the total weight of the composition.

7. The composition of claim 1, wherein said α-cyano-β,β-diphenylacrylate compound is present in an amount of at least about 0.5% by weight of the total weight of the composition.

8. The composition of claim 7, wherein said α-cyano-β,β-diphenylacrylate compound is present in an amount of about 1.0% to about 8% by weight of the total weight of the composition.

9. The composition of claim 8, wherein said α-cyano-β,β-diphenylacrylate compound comprises 2-ethylhexyl-2-cyano-3,3-diphenylacrylate.

10. The composition of claim 1, comprising a diester of formula (II) wherein $R^1$ and $R^2$ are 2-ethylhexane and p is 0.

11. The composition of claim 1, wherein said diester or polyester of naphthalene dicarboxylic acid is present in a range of about 0.1% to about 15% by weight of the total weight of the composition.

12. The composition of claim 1, wherein the weight ratio of (a) to (b) is in the range of about 1/1 to about 2/1.

13. The composition of claim 1, further comprising a methoxy-substituted benzophenone derivative.

14. The composition of claim 13, wherein said methoxy-substituted benzophenone derivative comprises benzophenone-3.

15. The composition of claim 13, wherein said methoxy-substituted benzophenone derivative is present in an amount of 0.5% or less by weight of the total weight of the composition.

16. The composition of claim 1, further comprising a photoactive compound selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts thereof; dihydroxy-naphthoic acid and salts thereof; o-hydroxydiphenyldisulfonate and salts thereof; p-hydroxydiphenyldisulfonate and salts thereof; coumarin and derivatives thereof; diazole derivatives; quinine derivatives and salts thereof; quinoline derivatives; hydroxy-substituted benzophenone derivatives; methoxy-substituted benzophenone derivatives; tannic acid; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

17. The composition of claim 16, wherein said photoactive compound comprises 2-ethylhexyl-p-methoxycinnamate.

18. The composition of claim 1, comprising an oil phase comprising said dibenzoylmethane derivative, said α-cyano-β,β-diphenylacrylate compound, said diester or polyester of naphthalene dicarboxylic acid, and a solvent system, wherein said solvent system comprises an effective amount of a polar solvent to increase the photostability of said dibenzoylmethane derivative and to increase the dielectric constant of the oil phase to at least about 7.

19. The composition of claim 18, wherein said oil phase has a dielectric constant of at least about 8.

20. The composition of claim 18, wherein the polar solvent comprises diethylhexyl malate, dimethyl capramide, or a combination thereof.

21. The composition of claim 18, wherein said dibenzoylmethane derivative is selected from the group consisting of 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

22. The composition of claim 21, wherein said dibenzoylmethane derivative is present in a range of about 0.1% to about 25% by weight of the total weight of the composition.

23. The composition of claim 21, wherein said α-cyano-β,β-diphenylacrylate compound comprises 2-ethylhexyl-2-cyano-3,3-diphenylacrylate.

24. A method of reducing contact of UV radiation with human skin comprising covering human skin with the composition of claim 1.

25. A method of reducing contact of UV radiation with human skin comprising covering human skin with the composition of claim 2.

26. A method of reducing contact of UV radiation with human skin comprising covering human skin with the composition of claim 3.

27. A method of reducing contact of UV radiation with human skin comprising covering human skin with the composition of claim 4.

28. A method of reducing contact of UV radiation with human skin comprising covering human skin with the composition of claim 13.

29. A method of reducing contact of UV radiation with human skin comprising covering human skin with the composition of claim 14.

30. A method of reducing contact of UV radiation with human skin comprising covering human skin with the composition of claim 15.

31. A method of reducing contact of UV radiation with human skin comprising covering human skin with the composition of claim 16.

32. A method of reducing contact of UV radiation with human skin comprising covering human skin with the composition of claim 17.

* * * * *

UNITED STATES PATENT AND TRADEMARK OFFICE
CERTIFICATE OF CORRECTION

PATENT NO. : 6,899,866 B2  Page 1 of 1
APPLICATION NO. : 10/785271
DATED : May 31, 2005
INVENTOR(S) : Craig A. Bonda et al.

It is certified that error appears in the above-identified patent and that said Letters Patent is hereby corrected as shown below:

On Title page Item 54 col. 1, "NAPHITHALATE" should be --NAPHTHALATE--.

On Title page Item 75 col. 1, add --Gary A. Neudahl, Cary, IL--.

Col. 17 in Claim 16, line 62, "quinine derivatives" should be --quinine--.

Signed and Sealed this

Fourteenth Day of November, 2006

JON W. DUDAS
*Director of the United States Patent and Trademark Office*